United States Patent
Lambert et al.

(10) Patent No.: US 8,377,705 B2
(45) Date of Patent: Feb. 19, 2013

(54) BREATH ANALYZER SYSTEM AND METHOD OF OPERATING THE SAME

(75) Inventors: David K. Lambert, Sterling Heights, MI (US); Michel F. Sultan, Troy, MI (US)

(73) Assignee: Delphi Technologies, Inc., Troy, MI (US)

(*) Notice: Subject to any disclaimer, the term of this patent is extended or adjusted under 35 U.S.C. 154(b) by 486 days.

(21) Appl. No.: 12/688,164

(22) Filed: Jan. 15, 2010

(65) Prior Publication Data

US 2010/0188232 A1 Jul. 29, 2010

Related U.S. Application Data

(60) Provisional application No. 61/206,257, filed on Jan. 29, 2009.

(51) Int. Cl.
*G01N 1/22* (2006.01)
(52) U.S. Cl. ........ 436/132; 436/167; 436/171; 436/900; 422/82.05; 422/82.09; 422/83; 422/84
(58) Field of Classification Search .............. 422/82.05, 422/82.09, 83, 84; 436/132, 167, 171, 900
See application file for complete search history.

(56) References Cited

U.S. PATENT DOCUMENTS

| | | | |
|---|---|---|---|
| 6,811,751 | B1 | 11/2004 | Olsson et al. |
| 7,095,501 | B2 | 8/2006 | Lambert et al. |
| 7,279,132 | B2 | 10/2007 | Sultan et al. |
| 2006/0153740 | A1 | 7/2006 | Sultan et al. |
| 2006/0154377 | A1 | 7/2006 | Lambert et al. |
| 2007/0077176 | A1 | 4/2007 | Lambert et al. |
| 2007/0296601 | A1 | 12/2007 | Sultan et al. |
| 2009/0087920 | A1 | 4/2009 | Pettersson et al. |

OTHER PUBLICATIONS

European Search Report dated Apr. 29, 2010.

*Primary Examiner* — Lyle Alexander
(74) *Attorney, Agent, or Firm* — Lawrence D. Hazelton

(57) ABSTRACT

A breath analyzer system and method for determining an estimate of blood alcohol concentration of a person. A light source projects light into a sampling region where breath from the person is expected. A first light detector and a second light detector are configured to detect light intensity of light having certain wavelengths at a first time and a second time. Signals from the light detectors at the first time and the second time are used to determine an estimate of the blood alcohol concentration of the person by determining a ratio of a first light detector signal change to a second light detector signal change.

19 Claims, 3 Drawing Sheets

BREATH ANALYZER SYSTEM AND METHOD OF OPERATING THE SAME

CROSS-REFERENCE TO RELATED APPLICATION

This application claims the benefit under 35 U.S.C. §119 (e) of U.S. Provisional Patent Application No. 61/206,257, filed Jan. 29, 2009, the entire disclosure of which is hereby incorporated herein by reference.

TECHNICAL FIELD OF INVENTION

The present invention generally relates to a chemical vapor sensor, and more particularly, to a chemical vapor sensor for estimating the blood alcohol concentration of a person.

BACKGROUND OF INVENTION

Vehicle crashes caused by drunk drivers have been a concern for many years. It has been proposed to equip vehicles with blood alcohol concentration (BAC) sensors to estimate the BAC of a person attempting to operate a vehicle based on the concentration of ethanol gas in the breath of the person. One conventional method to measure BAC of a person requires the person to fully exhale into a mouthpiece coupled to an apparatus that uses a fuel cell sensor to measure the ethanol vapor concentration in the exhaled breath emerging near the end of the exhalation. However, some people find this unpleasant. Other conventional methods and apparatus for measuring BAC do not require a person to exhale into a mouthpiece, but rely generally on a valve to route a second source of air without exhaled breath or without ethanol gas to serve as a baseline for determining ethanol gas concentration. Other methods rely on complicated signal analysis techniques that compare waveforms from an ethanol gas detector and a carbon dioxide gas detector. Moreover, some methods require a period time on the order of a minute to output an estimate of BAC and are sensitive to ambient concentrations of ethanol vapor such as from an intoxicated passenger or spilled ethanol fuel.

SUMMARY OF THE INVENTION

In accordance with one aspect of this invention, a breath analyzer system is provided. The system is directed at determining an estimate of the blood alcohol concentration of a person. The system includes a light source, a first light detector, a second light detector, and a controller. The light source is configured to project light into a sampling region where breath from the person is expected. The first light detector is configured to detect a first light intensity of light emanating from the sampling region at an ethanol gas absorption wavelength and output an ethanol gas signal indicative of an ethanol gas concentration in the sampling region. The second light detector is configured to detect a second light intensity of light emanating from the sampling region at a trace gas absorption wavelength and output a trace gas signal indicative of a trace gas concentration in the sampling region. The controller is configured to receive a first ethanol gas signal and a first trace gas signal at a first time and receive a second ethanol gas signal and a second trace gas signal at a second time distinct from the first time. The controller is also configured to determine an estimate of the blood alcohol concentration of the person based on the first ethanol gas signal, the second ethanol gas signal, the first trace gas signal, and the second trace gas signal.

In another aspect of the present invention, a breath analyzer system is provided. The system is directed at determining an estimate of blood alcohol concentration of a person. The system includes a light source, a first light detector, a second light detector, and a controller. The light source is configured to project light into a sampling region where breath from the person is expected. The first light detector is configured to detect a first light intensity of light emanating from the sampling region at an ethanol gas absorption wavelength and output an ethanol gas signal indicative of an ethanol gas concentration in the sampling region. The second light detector is configured to detect a second light intensity of light emanating from the sampling region at a carbon dioxide gas absorption wavelength and output a carbon dioxide gas signal indicative of a carbon dioxide gas concentration in the sampling region. The controller is configured to receive a first ethanol gas signal and a first carbon dioxide gas signal at a first time and receive a second ethanol gas signal and a second carbon dioxide gas signal at a second time distinct from the first time. The controller is further configured to determine an ethanol gas signal change based on a difference of the first ethanol gas signal and the second ethanol gas signal and determine a carbon dioxide gas signal change based on a difference of the first carbon dioxide gas signal and the second carbon dioxide gas signal. The controller is also configured to determine an estimate of the blood alcohol concentration of the person based on a ratio of the ethanol gas signal change to the carbon dioxide gas signal change when the carbon dioxide gas signal change is greater than a threshold.

In yet another aspect of the present invention, a method of operating a breath analyzer system is provided. The method is directed at determining an estimate of blood alcohol concentration of a person. The breath analyzer system comprises a light source configured to project light into a sampling region where breath from the person is expected, a first light detector configured to detect a first light intensity of light emanating from the sampling region at an ethanol gas absorption wavelength and output an ethanol gas signal indicative of an ethanol gas concentration in the sampling region, a second light detector configured to detect a second light intensity of light emanating from the sampling region at a trace gas absorption wavelength and output a trace gas signal indicative of a trace gas concentration in the sampling region, and a controller configured to receive the ethanol gas signal and the trace gas signal. The method includes the steps of receiving a first ethanol gas signal and a first trace gas signal at a first time, and receiving a second ethanol gas signal and a second trace gas signal at a second time distinct from the first time. The method also includes the step of and determining an estimate of the blood alcohol concentration of the person based on the first ethanol gas signal, the second ethanol gas signal, the first trace gas signal, and the second trace gas signal.

Further features and advantages of the invention will appear more clearly on a reading of the following detailed description of the preferred embodiment of the invention, which is given by way of non-limiting example only and with reference to the accompanying drawings.

BRIEF DESCRIPTION OF DRAWINGS

The present invention will now be described, by way of example with reference to the accompanying drawings, in which.

DETAILED DESCRIPTION OF INVENTION

Figure 1:
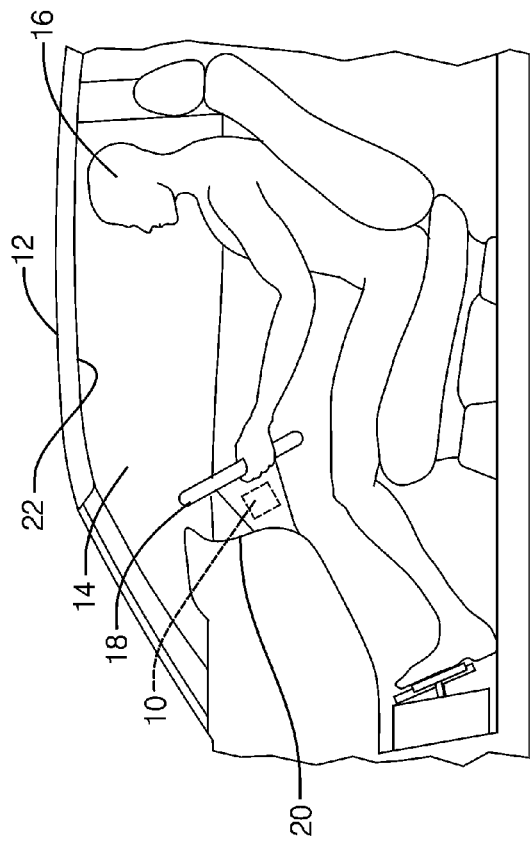
FIG. 1 is a cut-away view of a vehicle with a breath analyzer system in accordance with one embodiment.

In accordance with an embodiment of a breath analyzer system, FIG. 1 illustrates an exemplary, non-limiting embodiment of a breath analyzer system 10 employed in a vehicle 12. The system 10 is shown arranged in the vehicle 12 to measure concentrations of gaseous chemicals such as an ethanol gas concentration of air in a vehicle cabin 14. The ethanol gas concentration may be useful for estimating the blood alcohol concentration (BAC) of a person 16 residing in the cabin 14. The BAC of the person 16 may indicate that the person 16 has recently consumed an alcoholic beverage. It may be desirable to determine the BAC of the person 16 attempting to operate the vehicle 12 to inform the person 16 that their BAC may be greater than a BAC threshold, either one set by law or predetermined by the vehicle owner.

In the illustrated embodiment, the system 10 is part of a steering wheel assembly 18 so as to be proximate to an area or sampling region that may receive some of the breath exhaled by the person 16. In one embodiment, a puff of breath exhaled by the person 16 toward the system 10 is drawn through an aperture for sampling by the system 10. Alternately, the system 10 may be coupled to a dash 20 or a headliner 22. It should be appreciated that the breath analyzer system 10 may be used in other arrangements such as a stand alone or portable device for estimating the BAC of a person 16 at locations other then in the vehicle cabin 14. As will be explained below, the system 10 is able to determine the percentage of an air sample that is from exhaled breath to make an estimate of BAC. As such, the person is not required to full exhale into a mouthpiece. It should be appreciated by those skilled in the art that the description herein is not limited to estimating the BAC of the person 16 and may be used to detect a gas concentration other than ethanol gas.

Exemplary chemical vapor sensors are disclosed in commonly assigned U.S. Pat. No. 7,279,132 entitled "CHEMICAL VAPOR SENSOR HAVING AN ACTIVE AND A PASSIVE MEASUREMENT MODE," U.S. Pat. No. 7,095,501 entitled "ETHYL ALCOHOL SENSOR AND METHOD OF USE," U.S. Patent Application Publication No. 2007/0077176 entitled "TRACER TO COMPENSATE FOR ENVIRONMENTAL VARIATIONS THAT INFLUENCE A CHEMICAL VAPOR SENSOR MEASUREMENT," and U.S. Patent Application Publication No. 2006/0154377 entitled "CHEMICAL VAPOR SENSOR," the entire disclosures of which are hereby incorporated herein by reference. A method and apparatus for estimating blood alcohol concentration (BAC) of a person is also described in U.S. Pat. No. 6,811,751 to Olsson et al. which is also hereby incorporated herein by reference.

Figure 2:
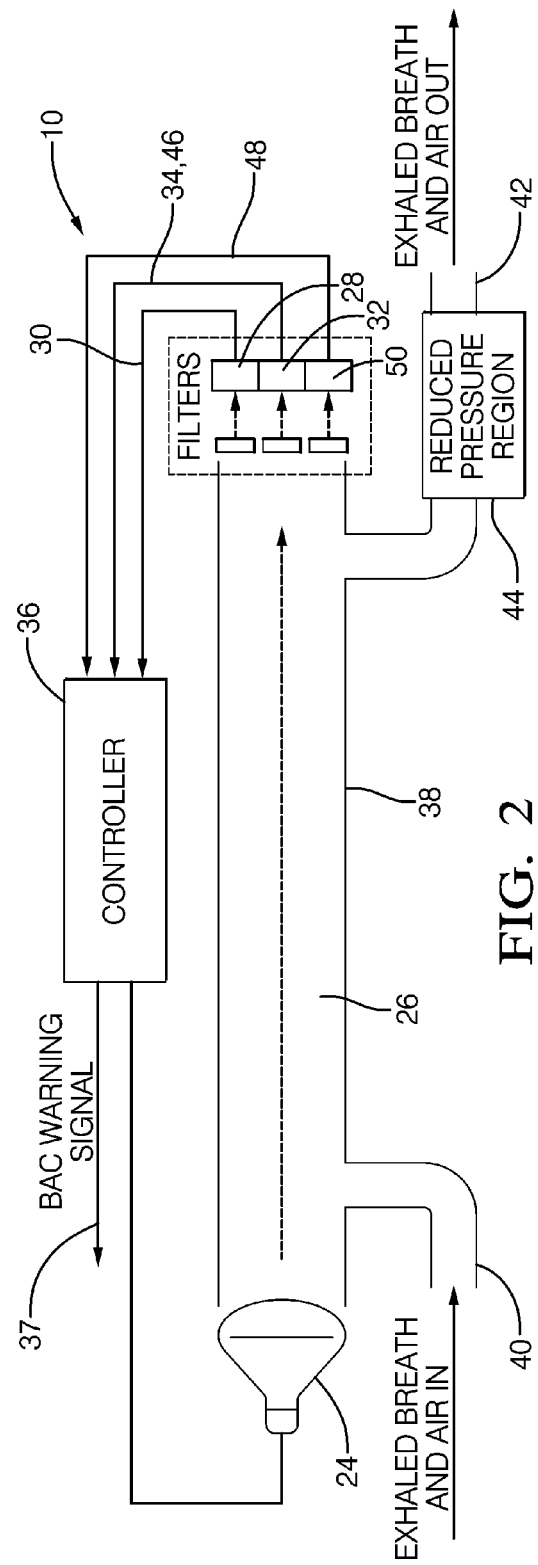
FIG. 2 is a block diagram of a breath analyzer system in accordance with one embodiment.

FIG. 2 illustrates a block diagram of an embodiment of the breath analyzer system 10. The system 10 includes a light source 24 configured to project light into a sampling region 26 where exhaled breath from the person 16 is expected. The system 10 may sense a particular gas by determining that light transmitted at a particular wavelength corresponding to the light absorption wavelength of the particular gas has a reduced intensity.

The light source 24 preferably emits light at the wavelength corresponding to the absorption wavelength of the gas of interest. As used herein, light includes any form of electromagnetic energy. According to one embodiment, the light source 24 is an infrared (IR) light source. If more than one gas is being detected, then the light source 24 should emit light at wavelengths corresponding to at least the gases of interest. The light source 24 may suitably output light comprising a range or band of wavelengths. For example, the light source 24 may be an infrared light source such as an Axetris EMIRS 200, an International Light Technologies lamp models L1010 or L1040, an incandescent lamp, or an electrically heated element.

The system 10 also includes a first light detector 28 configured to detect a first light intensity of light at a particular wavelength that is emanating from the sampling region 26. The light detected by the first light detector 28 may be solely from the light source 24, or may include light from other sources such as the sun or vehicle interior lights. The first light detector may be a thermopile infrared detector covered by an interference filter that transmits a band centered at the wavelength of interest. In one embodiment, the first light detector 28 may be configured to detect an intensity of light at an ethanol gas absorption wavelength for detecting the presence of ethanol gas in the sampling region 26.

It has been observed that the first light intensity at an ethanol gas absorption wavelength decreases as ethanol gas concentration increases, and so may be useful for detecting ethanol gas exhaled by the person 16. A suitable absorption wavelength for detecting ethanol vapor is 3.36 micrometers ($\mu m$). For purposes of explanation and not limitation, a suitable first light detector 28 may include a filter (e.g., bandpass filter) such as a Dexter Research part number FHC1. Such a filter allows more light at or near a wavelength of 3.36 $\mu m$ to pass than light at other wavelengths. By including such a filter, the first light detector 28 may be configured to detect ethanol gas concentration. The first light detector 28 may also be configured to output an ethanol gas signal 30 corresponding to the first light intensity of light at an ethanol gas absorption wavelength.

The system 10 may also include a second light detector 32 configured to detect a second light intensity of light at a trace gas absorption wavelength emanating from the sampling region 26. The light detected by the second light detector 32 may be solely from the light source 24, or may include light from other sources. It has been observed that carbon dioxide and water vapor are present in exhaled breath from the person 16 at concentration levels that are generally higher than the concentration levels present in the air being inhaled by the person 16, and so may be suitable trace gas candidates.

A suitable absorption wavelength for detecting carbon dioxide is around 4.4 micrometers ($\mu m$). As such, one embodiment of the second light detector 32 may include a filter (e.g., bandpass filter) such as a model NB-4420-080 from Spectrogon. Such a filter allows more light at a wavelength of 4.4 $\mu m$ to pass than light at other wavelengths. By including such a filter, the second light detector 32 may be configured to detect carbon dioxide gas concentration. The second light detector 32 may be further configured to output a trace gas signal 34 indicative of a trace gas concentration in the sampling region 26. For the embodiment configured to detect carbon dioxide, the second light detector 32 would then be configured to output a carbon dioxide signal 46 corresponding to the intensity of light at a carbon dioxide gas absorption wavelength, whereby the first trace gas signal VT1 is a first carbon dioxide signal VT1 and the second trace gas signal VT2 is a second carbon dioxide signal VT2, The first and second light detectors 28 and 32 may each include an infrared detector, particularly for the embodiment in which the light source is an infrared light source. While two distinct light detectors 28 and 32 are shown and described herein according to the present embodiment, it should be appreciated that both detectors could be integrally provided in a single device, such as a dual-element thermopile detector which may include filters for filtering the wavelengths of interest, according to other embodiments. Furthermore, light intensity at two or more wavelengths may be detected by a single element detector combined with a means to change the filter characteristic such as moving various filters between the light source 24 and the single element detector.

Exhaled breath may include trace gases such as carbon dioxide and water vapor at concentration levels higher than the air being inhaled by the person 16. By determining a trace gas concentration of the gas in the sampling region 26, a percentage of exhaled breath in the sampling region 26 can be determined. If the percentage of exhaled breath in the sampling region 26 is known, the concentration of ethanol gas in the sampling region 26 can be used to estimate the concentration of ethanol gas in the exhaled breath from the person 16. The ethanol gas concentration in exhaled breath may be used to estimate the blood alcohol concentration (BAC) of the person 16.

FIG. 2 further illustrates one embodiment of the breath analyzer system 10 having a controller 36 configured to receive the ethanol gas signal 30 and the trace gas signal 34. The controller 36 may include a microprocessor or other control circuitry as should be evident to those in the art. The controller may include memory, including non-volatile memory, such as electrically erasable programmable read-only memory (EEPROM) for storing one or more routines, thresholds and captured data. The one or more routines may be executed by the microprocessor to perform steps for determining an estimate of blood alcohol concentration of a person as described herein. It has been observed that the ethanol gas signal 30 and the trace gas signal 34 vary over time in response to inhaling and exhaling of breath by the person 16. It was discovered that the variation of the trace gas signal could be used to indicate that exhaled breath is present and compensate an ethanol gas concentration measurement so that a sample of reference air or baseline air free of ethanol gas and/or free of exhaled breath is not necessary. If the values of the ethanol gas signal 30 and the trace gas signal 34 are recorded at substantially the same moments in time, then the ethanol gas concentration may be determined.

Figure 3:
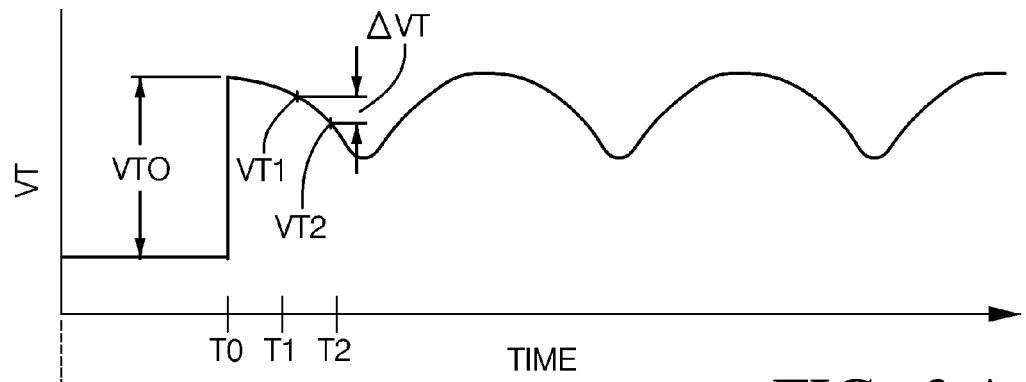
FIG. 3 is three graphs depicting exemplary signals from light detectors in the breath analyzer system of FIG. 2 in accordance with one embodiment.
Figure 3:
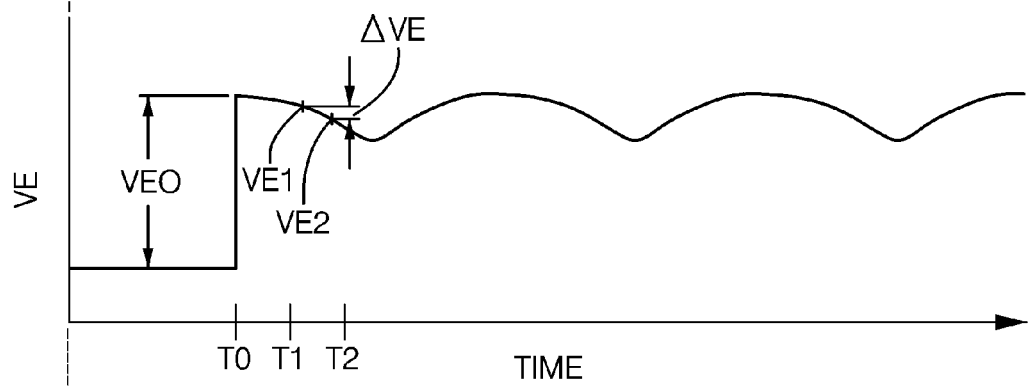
Figure 3:
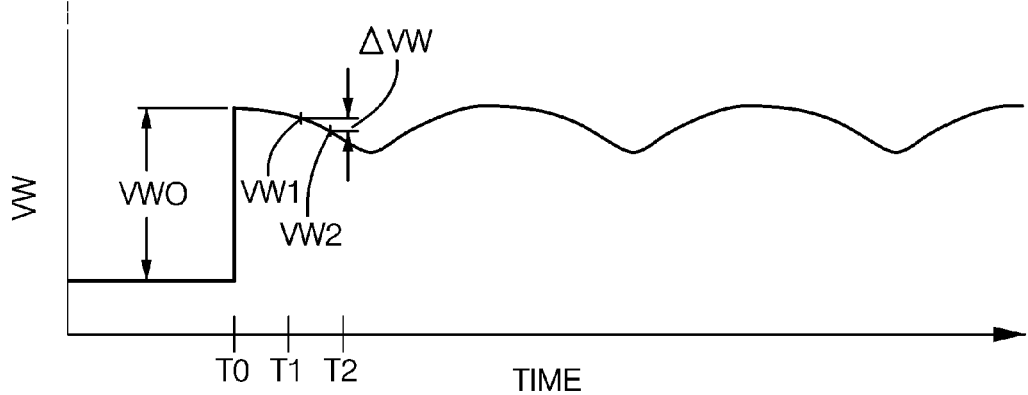

FIG. 3 illustrates exemplary waveforms for the ethanol gas signal 30 (VE) and the trace gas signal 34 (VT). At time T0 the light source 24 is switched from an off state to an on state. Following time T0, the signals VE and VT vary in response to respiration of the person 16. As the person 16 exhales, the concentrations of trace gas and ethanol gas (if present) typically increase, thereby absorbing more light at the corresponding absorption wavelengths and causing the values of signals VE and VT to decrease. The increasing concentrations may be due to gas drawn entering the sampling region 26 having a higher percentage of exhaled breath. After the person 16 exhales, typically the person 16 inhales, so the concentrations of trace gas and ethanol gas in the sampling region 26 tend to decrease as illustrated by the values of VE and VT increasing. The decreasing concentrations may be due to gas drawn through the sampling region 26 by the reduced pressure region 44 having a lower percentage of exhaled breath, natural diffusion, or movement induced by air being circulated by the vehicle ventilation system.

One embodiment of the controller 36 may be configured to receive a first ethanol gas signal VE1 and a first trace gas signal VT1 sampled at substantially a first time T1, and receive a second ethanol gas signal VE2 and a second trace gas signal VT2 sampled at substantially a second time T2 distinct from the first time T1. As used herein, receiving gas signals sampled at substantially a specific time means that the signals are sampled close enough in time relative to each other so that the air in the sample region has substantially the same percentage of the various gases of interest when each sample is made. T1 is delayed after T0 a sufficient amount of time for the light source 24 to stabilize the output spectrum intensity.

It is desirable to estimate the BAC of a person 16 attempting to operate the vehicle 12 without the person 16 being undesirably delayed. To this end, light source 24 may be turned on as soon as the vehicle door is opened. Also, the light source 24 may be selected so its output is able to stabilize within the time the person 16 takes to enter the vehicle 12 and prepare to operate the vehicle 12. T2 is preferably delayed after T1 by an amount of time sufficient for a significant portion of an exhalation. The controller may be further configured to determine a respiration pattern of a person so that the times T1 and T2 are during a single exhale event. As such, T2 cannot be delayed so long so as to be at or after the minimum value of VT and VE which corresponds to the end of exhaling and the beginning of inhaling by the person. For example, if a typical respiration rate for a human is 20 breaths per minute, then an exemplary time delay between T1 and T2 may be about 0.75 seconds.

It should be appreciated that when exhalation is under the conscious control, the person 16 may choose to hold their breath for a period of time after entering the vehicle, so it is advantageous to continue sampling and checking for a change in the values of VT. The controller 36 may use a sample rate that is much higher than the respiration rate so optimum values of VT and VE may be selected. Alternately, the controller 36 may analyze the respiration waveforms for VT and select T1 and T2 based on a determination of an exhale event. A respiration pattern may also be determined by detecting trace gas concentration maximums and minimums. As such, it may also be advantageous for T1 to be selected to be delayed a period of time after the exhale event begins, 0.25 seconds for example. It is understood that the controller 36 may continue to record values of VT and VE over several respiration cycles until certain conditions are met.

The controller 36 may then determine an estimate of the blood alcohol concentration of the person based on the first ethanol gas signal VE1, the second ethanol gas signal VE2, the first trace gas signal VT1, and the second trace gas signal VT2. In one non-limiting embodiment, the controller 36 may first determine an ethanol gas signal change ΔVE based on a difference of the first ethanol gas signal VE1 and the second ethanol gas signal VE2, determine a trace gas signal change ΔVT based on a difference of the first trace gas signal VT1 and the second trace gas signal VT2. An estimate of the BAC of the person 16 may be made using Equation 1.

$$BAC = K*(\Delta VE/\Delta VT) \qquad \text{Equation 1}$$

In Equation 1, K is an empirically determined constant that is influenced by a variety of factors such as the chemical species being sensed, the ratio of light intensity emitted by light source 24 at the two wavelengths, and the transmission spectra of the filters that cover the first light detector 28 and the second light detector 32. It is advantageous to use the differences of readings at times T1 and T2 to determine gas concentration because it avoids the need to provide a reference or base line gas supply to the sampling region 26 so measurements that are free of ethanol gas or known to have a certain trace gas concentrations can be made. If the light detectors are thermopile detectors, it is also advantageous to use the difference between outputs at times T1 and T2, because it reduces the effect of a slowly varying baseline voltage, added to the light induced output voltage, that may be present in the output of a thermopile detector. Such a baseline voltage may, for example, be caused by a gradual drift in the ambient temperature over time.

In another embodiment, the controller 36 may be further configured to only determine an estimate of the BAC of the person 16 when the trace gas signal change ΔVT is greater than a threshold. The magnitude of the trace gas signal change ΔVT may be used as an indicator that the percentage of exhaled breath in the sampling region 26 is sufficient to allow the BAC to be reliably estimated.

In another embodiment, the system 10 may be configured to switch the light source 24 off and on. As such, when the light source 24 is switched off, the light source does not project light into the sampling region 26. When the light source 24 is switched on, the light source 24 projects light into the sampling region 26. The controller 36 may be configured to receive a light-off ethanol gas signal and a light-off trace gas signal when the light is off and receive a light-on ethanol gas signal and a light-on trace gas signal when the light is on. The light-on and light-off signals may be used to compensate for the spectral intensity of the light output by the light source 24 varying with age or ambient temperature, or for optical devices such as lenses or filters located between the light source 24 and the detectors 28, 32, and 50 being dirty or otherwise obstructed, or for variation in the power supplied to the light source 24. The light-on and light-off signals may also be used to compensate for the presence of ambient light in the light received by the light detectors 28, 32, and 50. In one non-limiting example, the controller 36 may determine an ethanol gas signal offset VEO based on a difference of the light-on ethanol gas signal and the light-off ethanol gas signal, determine a trace gas signal offset VTO based on a difference of the light-on trace gas signal and the light-off trace gas signal, and determine a calibration constant based on a ratio of the ethanol gas signal offset VEO and the trace gas signal offset VTO and thereby calibrate the system. This calibration constant may be incorporated into Equation 1 as shown in Equation 2. Like K in Equation 1, C in Equation 2 is an empirically determined constant that is influenced by a variety of factors.

$$BAC = C*(VTO/VEO)*(\Delta VE/\Delta VT) \qquad \text{Equation 2}$$

In another embodiment, the controller 36 is further configured to output a blood alcohol warning signal 37 when the estimate of the blood alcohol concentration (BAC) of the person 16 is greater than a BAC threshold. The BAC threshold may correspond to a threshold determined by law, or may be a threshold selected by the vehicle owner. The blood alcohol warning signal 37 may activate an indicator light, or may be used to warn the person 16 (e.g., driver) and/or disable the vehicle and thereby prevent the person 16 from operating the vehicle.

FIG. 2 further illustrates an embodiment of the system 10 having a tube 38 that includes an inlet 40 and an outlet 42 along the length of the tube 38 for guiding a sample of gas comprising exhaled breath from the person 16 and/or ambient air through the sampling region 26. In this non-limiting embodiment, the light source 24 is arranged at one end of the tube 38, and the first light detector 28 and the second light detector 32 are arranged at the other end of the tube 38. The system may also include a reduced pressure region 44 coupled to the outlet 42 for inducing flow through the tube 38 so that the air in sampling region 26 is refreshed. The reduced pressure region 44 may be provided by an active device, such as a fan or pump such that air is drawn through the sampling region 26.

In another non-limiting embodiment, system 10 may include a mirror (not shown) arranged to reflect light from the light source 24 toward the first light detector 26 and the second light detector 32. By including a minor, the light source 24, the first light detector 26, and the second light detector 32 may be arranged near each other such that light from the light source 24 to the minor and light reflected by the mirror toward the first light detector 26 and the second light detector 32 traverse substantially the same path. Such an arrangement may have a region that is not defined by a tube, but may be an open region where breath exhaled by the person 16 may pass.

In one embodiment the trace gas may be selected to be carbon dioxide (CO2). For CO2 as the trace gas (Ta), Equation 2 may be rewritten as Equation 3. Selecting carbon dioxide as the trace gas is advantageous because the carbon dioxide concentration of ambient air is relatively constant. However, it is noted that the ethanol gas concentration in exhaled breath is dependent on the body temperature of the person 16. Also, the carbon dioxide concentration in exhaled breath may be influenced by certain medical conditions. Ca is empirically determined specifically for the case where the trace gas is CO2.

$$BACa = Ca*(VTaO/VEO)*(\Delta VE/\Delta VTa) \qquad \text{Equation 3}$$

In another embodiment the trace gas may be selected to be water vapor (H2O). For H2O as the tracer gas (Tb), Equation 2 may be rewritten as Equation 4. Selecting water vapor as a trace gas is advantageous in that helps cancel out the effect of body temperature on the concentration of ethanol vapor at a given BAC. Cb is empirically determined specifically for the case where the tracer gas is H2O.

$$BACb = Cb*(VTbO/VEO)*(\Delta VE/\Delta VTb) \qquad \text{Equation 4}$$

In another embodiment, the system 10 may use both carbon dioxide and water vapor as trace gases. In this embodiment the second light detector 32 may be configured to detect a second light intensity of light emanating from the sampling region 26 at a carbon dioxide absorption wavelength and output a carbon dioxide signal 46 indicative of a carbon dioxide concentration in the sampling region 26. The system 10 may further include a third light detector 50 configured to detect a third light intensity of light emanating from the sampling region 26 at a water vapor absorption wavelength and output a water vapor signal 48 indicative of a water vapor concentration in the sampling region 26. Waveforms for the carbon dioxide signal 46 and the water vapor signal 48 are generally similar in shape to the waveforms for the ethanol gas signal VE and the trace gas signal VT illustrated in FIG. 3. If the trace gas is carbon dioxide, then the graph for VT may be used to illustrate the carbon dioxide signal 46. In this embodiment, the controller 36 may be further configured to receive a first ethanol signal VE1, a first carbon dioxide signal VT1, and a first water vapor signal VW1 at the first time T1, receive a second ethanol signal VE2, a second carbon dioxide signal VT2, and a second water vapor signal VW2 at the second time T2, and determine an estimate of the blood alcohol concentration of the person based on the first ethanol gas signal VE1, the first carbon dioxide signal VT2, the first water vapor signal VW1, the second ethanol gas signal VE2, the second trace gas signal VT2, and the second water vapor signal VW2.

It is advantageous to include both the carbon dioxide gas signal 46 and the water vapor signal 48 in the determination of an estimate the BAC of a person 16 as using two independent tracers improves reliability and accuracy of the BAC estimate. For example, the concentration of ethanol vapor in exhaled breath generally depends on body temperature in a manner similar to the dependence of the concentration of water vapor in breath on body temperature. Also, there are medical conditions that may influence the CO2 concentration in exhaled breath. As such, there may be some uncertainty regarding the value of Ca for certain conditions, particularly when the person 16 is atypical of the population tested to determine Ca. Also, if the ambient temperature is close to body temperature, and the ambient humidity is close to 100%, the concentration of water vapor in exhaled breath is approximately the same in breath and in ambient air. As such, there may be some uncertainty regarding the value of Cb for certain conditions, particularly when ambient humidity and temperature differ from the calibration conditions used to determine Cb.

In one embodiment, the BACa from Equation 3 which is based on using CO2 as a trace gas and the BACb from Equation 4 which is based on using H2O as a trace gas may be combined to provide a better BAC estimate. One non-limiting example is to determine the uncertainty of Ca based on individual values of Ca for a variety of test persons, and calculate a standard deviation Sa of BACa. Likewise, the uncertainty of Cb may be determined by collecting Cb data for a number of environmental conditions and then calculating a standard deviation Sb of BACb. Then a weighted average may be calculated using Equation 5.

$$BAC=[(BACa/Sa^2)+(BACb/Sb^2)]/[(1/Sa^2)+(1/Sb^2)] \quad \text{Equation 5}$$

If both BACa and BACb are valid measurements, the standard deviation of BAC from Equation 5 is less than Sa or Sb. Alternatively, BAC may be selected to be one of BACa from Equation 3 or BACb from Equation 4, based on predetermined criteria, which may be based on one or more of the ambient temperature, the settings of the air conditioning system, and the humidity of the air. Furthermore, the values of Sa and Sb may be adjusted as confidence in the value of Ca and Cb increases. For example, if it is believed that the same person is present for a period of time and the environmental conditions are such that the BACa and BACb values from Equations 3 and 4 are reliable, then the BACa and BACb values may be compared for consistency and adjustments may be made to the values of Ca and Cb.

Figure 4:
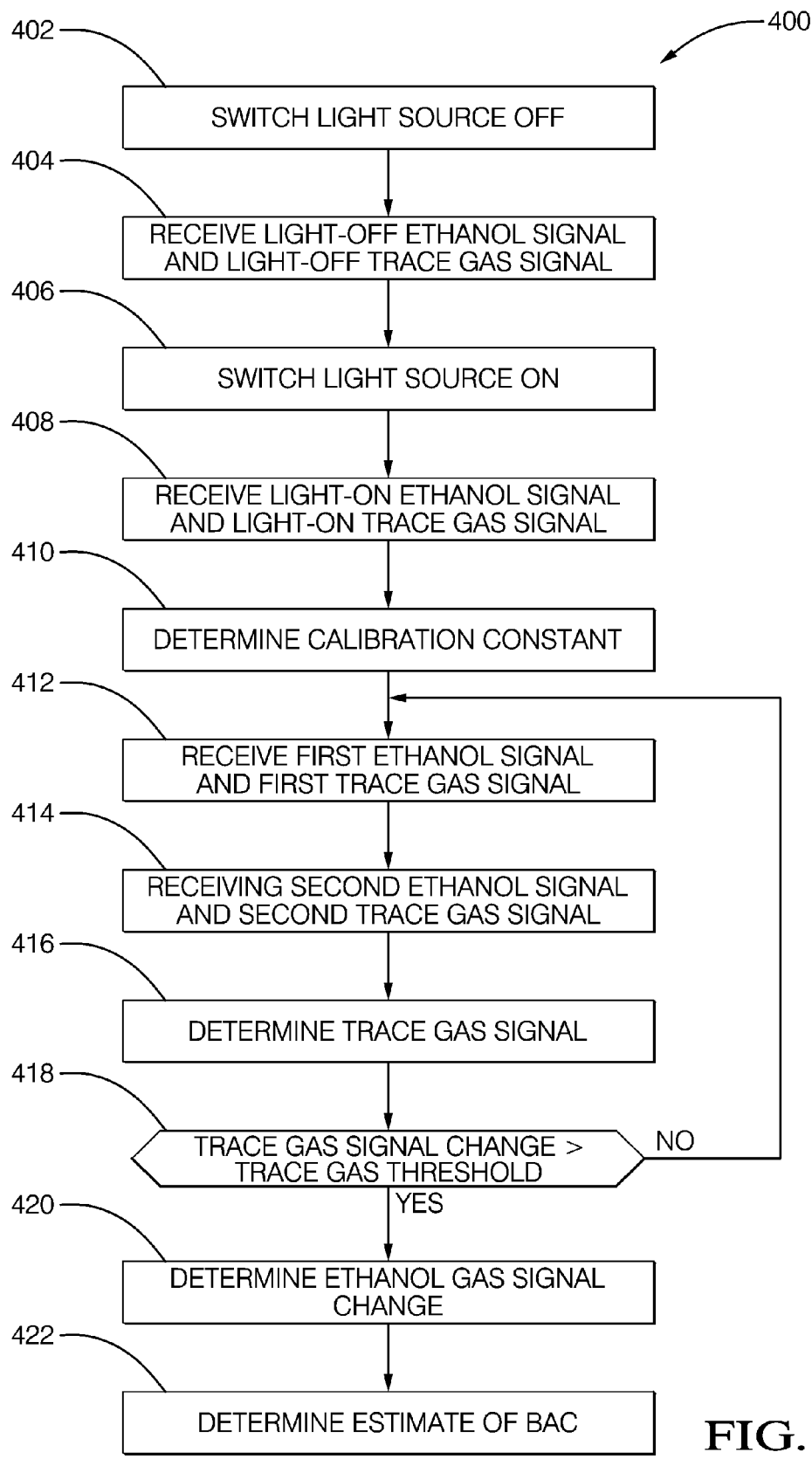
FIG. 4 is a flow chart illustrating a method of operating a breath analyzer system, in accordance with one embodiment.

FIG. 4 illustrates an embodiment of a method or routine 400 for operating a breath analyzer system 10 for determining an estimate of the blood alcohol concentration of a person 16. The method may include arranging a light source 24 to project light into a sampling region 26 where breath from the person is expected, and/or arranging a first light detector 28 and a second light detector 32 to detect the intensity of light emanating from the sampling region 26 at selected wavelengths. The light detected by the light detectors 28 and 32 may be solely from the light source 24, or may include light from other sources. At step 402 of method 400, the light source 24 is switched off. In one non-limiting embodiment, the light source 24 is switched off and on by the controller 36. Alternately, the light source 24 may be switched off and on by a vehicle ignition switch. Switching off the light source 24 may occur periodically while the vehicle is running, or may occur when the vehicle is switched off. While the light is off, prior to time T0, the first light detector 28 outputs a light-off ethanol gas signal, and the second light detector 32 outputs a light-off trace gas signal. These light-off signals may be used as indicators of how much of the light received by the detectors 28 and 32 is ambient light and therefore not from the light source 24. If light detectors 28 and 32 are thermopiles, the use of a difference between light-on and light-off signals may reduce the effect of a slowly varying baseline on the measurement.

At step 404, the controller 36 receives the light-off ethanol gas signal and the light-off trace gas signal. At step 406 and at a time corresponding to T0, the light source 24 is switched on. At step 408, the light-on ethanol gas signal and the light-on trace gas signal are received by the controller 36. The difference between the light-off trace gas signal and the light-on trace gas signal is used to determine the value of VTO as illustrated in FIG. 3. Likewise, the difference between the light-off ethanol gas signal and the light-on ethanol gas signal is used to determine the value of VEO. If these light-off and light-on measurements are repeated on a periodic basis, then the system 10 may be able to compensate for changes in the amount of ambient light present in the light detected by the light detectors 28, 32, and 50. At step 410, at or after time T0, a calibration constant is determined. The calibration constant may be used to compensate the system 10 for variations in the intensity of light output by the light source 24. One example of a calibration constant is based on a ratio of the ethanol gas signal offset VEO and the trace gas signal offset VTO as suggested in Equation 2.

At time T1, as illustrated in FIG. 3, the first light detector 28 outputs a first ethanol gas signal VE1, and the second light detector 32 outputs a first trace gas signal VT1. At step 412, the controller 36 receives the first ethanol gas signal VE1 and the first trace gas signal VT1. At time T2 subsequent to time T1, the first light detector 28 outputs a second ethanol gas signal VE2, and the second light detector 32 outputs a second trace gas signal VT2. At step 414, the controller 36 receives the second ethanol gas signal VE2 and the second trace gas signal VT2. At step 416, the controller 36 determines a trace gas signal change $\Delta VT$ based on a difference of the first trace gas signal and the second trace gas signal. At step 418, if the trace gas signal change $\Delta VT$ is greater than a trace gas threshold, then there may be a sufficient percentage of exhaled breath present in the sampling region 26 so that a reliable estimate of BAC of the person 16 may be made, so the method 400 proceeds to step 420. If the trace gas signal change $\Delta VT$ is less than the trace gas threshold, then there may be an insufficient percentage of exhaled breath present in the sampling region 26, so the method 400 may return to step 412 to repeat the measurement process. In another embodiment, if the trace gas signal change $\Delta VT$ is less than the trace gas threshold, the method 400 may return to step 402 and include the calibration process. In still another embodiment, if the trace gas signal change $\Delta VT$ is less than the trace gas threshold, the system 10 may output an indication that there is insufficient exhaled breath, such as turning on an indicator light.

At step 420, the controller 36 determines an ethanol gas signal change $\Delta VE$ based on a difference of the first ethanol gas signal VE1 and the second ethanol gas signal VE2. At step 422, the controller 36 determines an estimate of the blood alcohol concentration of the person using Equation 2.

Accordingly, a system 10 and method 400 for estimating the blood alcohol concentration (BAC) of a person are provided. A sampling region 26 of space expected to comprise exhaled breath of the person 16 is illuminated by a light source 24, and the intensity of light at selected wavelengths emanating from the sampling region 26 is measured. The concentration of exhaled breath varies correspondingly with the respiration of the person 16. The wavelengths are selected to correspond to the absorption wavelengths of ethanol gas and a trace gas that is typically present in exhaled breath. The system measures the intensity of light at selected wavelengths at two distinct times. Respiration or more specifically exhalation by the person 16 causes variation in the ethanol gas (if present) and trace gas concentrations. Thus the BAC measurement is generally specific to the person 16 residing in close proximity to the system 10. By determining differences of light intensities at two distinct times, the system can discern the percentage of ethanol gas concentration that is from breath exhaled by the person 16 from the percentage of ethanol gas that is from ambient air. By detecting variations due to breathing, the system 10 advantageously does not need complicated valves and secondary sources of air to make an estimate of BAC. By using measurements from two detectors at two moments in time, the system 10 does not need to perform a complicated analysis of the waveforms output by the ethanol gas detector and the trace gas detector. Furthermore, the system 10 can perform a self-calibration by comparing light intensities measured when the light source 24 is off to light intensities when the light source 24 is on.

It should be appreciated that when the person 16 supplies or directs a puff of breath toward the system, the BAC estimate is specific to that person 16. The estimate is generally unaffected by background sources of ethanol vapor such as an intoxicated passenger in the vehicle who is not in close proximity to the system 10 or spilled ethanol fuel. Also, the time duration of making an estimate of BAC is convenient to a vehicle operator since it is approximately the time for the driver to exhale a puff of breath. In addition, because of a self-calibration aspect of the invention, the measurement is generally unaffected by gradual changes in the optical system. Moreover, because the measurement uses the difference between detectors measurements closely spaced in time, it is suitable for use with thermopile detectors despite a slowly varying baseline voltage in the output of such detectors.

While this invention has been described in terms of the preferred embodiments thereof, it is not intended to be so limited, but rather only to the extent set forth in the claims that follow.

We claim:

1. A breath analyzer system for determining an estimate of blood alcohol concentration of a person, said system comprising:
    a light source configured to project light into a sampling region where breath from the person is expected;
    a first light detector configured to detect a first light intensity of light emanating from the sampling region at an ethanol gas absorption wavelength, said first light detector further configured to output an ethanol gas signal indicative of an ethanol gas concentration in the sampling region;
    a second light detector configured to detect a second light intensity of light emanating from the sampling region at a carbon dioxide absorption wavelength, said second light detector further configured to output a carbon dioxide signal indicative of a carbon dioxide concentration in the sampling region;
    a third light detector configured to detect a third light intensity of light emanating from the sampling region at a water vapor absorption wavelength and output a water vapor signal indicative of a water vapor concentration in the sampling region; and
    a controller programmed to receive a first ethanol gas signal, a first carbon dioxide signal, and a first water vapor signal sampled at substantially a first time, receive a second ethanol gas signal, a second carbon dioxide signal, and a second water vapor signal sampled at substantially a second time distinct from the first time, and determine an estimate of the blood alcohol concentration of the person based on the first ethanol gas signal, the second ethanol gas signal, the first carbon dioxide signal, the second carbon dioxide signal, the first water vapor signal, and the second water vapor signal.

2. The system in accordance with claim 1, wherein the controller is further configured to determine an ethanol gas signal change based on a difference of the first ethanol gas signal and the second ethanol gas signal, determine a carbon dioxide signal change based on a difference of the first carbon dioxide signal and the second carbon dioxide signal, determine a water vapor signal change based on a difference of the first water vapor signal and the second water vapor signal, and determine an estimate of the blood alcohol concentration of the person based on a ratio of the ethanol gas signal change to the carbon dioxide signal change and the water vapor signal change.

3. The system in accordance with claim 1, wherein the light source is configured to be switched off whereby the light source does not project light into the sampling region and switched on whereby the light source does project light into the sampling region, and the controller is configured to receive a light-off ethanol gas signal and a light-off carbon dioxide signal when the light is off, receive a light-on ethanol gas signal and a light-on carbon dioxide signal when the light is on, determine an ethanol gas signal offset based on a difference of the light-on ethanol gas signal and the light-off ethanol gas signal, determine a carbon dioxide signal offset based on a difference of the light-on carbon dioxide signal and the light-off carbon dioxide signal, and determine a calibration constant based on a ratio of the ethanol gas signal offset and the carbon dioxide signal offset and thereby calibrate the system.

4. The system in accordance with claim 1, said system further comprising a tube having an inlet and an outlet along the length of the tube for sampling the breath of the person, wherein the light source is arranged at one end of the tube, and the first light detector and the second light detector are arranged at the other end of the tube.

5. The system in accordance with claim 4, said system further comprising a reduced pressure region coupled to the outlet for inducing flow through the tube.

6. The system in accordance with claim 1, said system further comprising a mirror arranged to reflect light from the light source toward the first light detector and the second light detector, wherein the light source, the first light detector, and the second light detector are arranged together such that light from the light source to the minor and light reflected by the mirror toward the first light detector and the second light detector traverse substantially the same path.

7. The system in accordance with claim 1, wherein the controller is further configured to determine a carbon dioxide signal change based on a difference of the first carbon dioxide signal and the second carbon dioxide signal, and determine an estimate of the blood alcohol concentration of the person when the carbon dioxide signal change is greater than a threshold.

8. The system in accordance with claim 1, wherein the controller is further configured to output a blood alcohol warning signal when the estimate of the blood alcohol concentration of the person is greater than a threshold.

9. The system in accordance with claim 1, wherein the controller is further configured to select the first time and the second time to be during a single exhale event by the person.

10. The system in accordance with claim 1, wherein the light source comprises an infrared light source, and the first light detector, second light detector, and the third light detector each comprise an infrared detector.

11. The system in accordance with claim 1, wherein the first light detector comprises a first element of a thermopile detector, the second light detector comprises a second element of the thermopile detector, and the third light detector comprises a third element of the thermopile detector.

12. The system in accordance with claim 1, wherein the first light detector comprises a thermopile detector receiving light through a first filter and the second light detector comprises the thermopile detector receiving light through a second filter.

13. The system in accordance with claim 1, wherein the breath analyzer system is installed on a vehicle to analyze the blood alcohol concentration of a driver of the vehicle.

14. A method for determining an estimate of blood alcohol concentration of a person, said method comprising the steps of:
   projecting light into a sampling region where breath from the person is expected;
   detecting a first light intensity of light emanating from the sampling region at an ethanol gas absorption wavelength and outputting an ethanol gas signal indicative of an ethanol gas concentration in the sampling region;
   detecting a second light intensity of light emanating from the sampling region at a carbon dioxide absorption wavelength and outputting a carbon dioxide signal indicative of a carbon dioxide concentration in the sampling region;
   detecting a third light intensity of light emanating from the sampling region at a water vapor absorption wavelength and outputting a water vapor signal indicative of a water vapor concentration in the sampling region;
   processing a first ethanol gas signal, a first carbon dioxide signal, and a first water vapor signal sampled substantially at a first time;
   processing a second ethanol gas signal, a second carbon dioxide signal, and a second water vapor signal sampled substantially at a second time distinct from the first time; and
   determining an estimate of the blood alcohol concentration of the gas based on the first ethanol gas signal, the second ethanol gas signal, the first carbon dioxide signal, the second carbon dioxide signal, the first water vapor signal, and the second water vapor signal.

15. The method in accordance with claim 14, wherein the step of determining an estimate of the blood alcohol concentration of the person comprises the steps of:
   determining an ethanol gas signal change based on a difference of the first ethanol gas signal and the second ethanol gas signal;
   determining a carbon dioxide signal change based on a difference of the first carbon dioxide signal and the second carbon dioxide signal;
   determining an water vapor signal change based on a difference of the first water vapor signal and the second water vapor signal; and
   determining an estimate of the blood alcohol concentration of the person based on a ratio of the ethanol gas signal change to the carbon dioxide signal change and the water vapor signal change.

16. The method in accordance with claim 14, wherein the light source is configured to be switched off whereby the light does not project light into the sampling region and switched on whereby the light source does project light into the sampling region, said method further comprising the steps of:
   switching the light source off;
   receiving the light-off ethanol gas signal and the light-off carbon dioxide signal;
   switching the light source on;
   receiving the light-on ethanol gas signal and the light-on carbon dioxide signal;
   determining an ethanol gas signal offset based on a difference of the light-on ethanol gas signal and the light-off ethanol gas signal;
   determining a carbon dioxide signal offset based on a difference of the light-on carbon dioxide signal and the light-off carbon dioxide signal; and
   determining a calibration constant based on a ratio of the ethanol gas signal offset and the carbon dioxide signal offset and thereby calibrating the system.

17. The method in accordance with claim 14, wherein the step of determining an estimate of the blood alcohol concentration of the person is performed when a difference of the first carbon dioxide signal and the second carbon dioxide signal is greater than a threshold.

18. The method in accordance with claim 14, said method further comprising the step of outputting a blood alcohol warning signal when the estimate of the blood alcohol concentration of the person is greater than a BAC threshold.

19. The method in accordance with claim 14, said method further comprising the step of selecting the first time and the second time to be during a single exhale event by the person.

* * * * *